(12) United States Patent
Nakazawa et al.

(10) Patent No.: US 6,605,257 B1
(45) Date of Patent: Aug. 12, 2003

(54) MICRO ARRAY MANUFACTURING APPARATUS

(75) Inventors: Touji Nakazawa, Tokyo (JP); Akihiro Iimura, Tokyo (JP); Hideo Tashiro, Wako (JP); Tokuji Kitsunai, Wako (JP); Yoshihide Hayashizaki, Tsukuba (JP)

(73) Assignees: THK Co., LTD, Tokyo (JP); Riken, Wako (JP)

( * ) Notice: Subject to any disclaimer, the term of this patent is extended or adjusted under 35 U.S.C. 154(b) by 249 days.

(21) Appl. No.: 09/634,875

(22) Filed: Aug. 7, 2000

(30) Foreign Application Priority Data

Aug. 9, 1999 (JP) ............................................ 11-225060
Aug. 9, 1999 (JP) ............................................ 11-225061

(51) Int. Cl.$^7$ .............................. B01L 3/02; B01L 3/00; B01L 9/00; G01N 21/00; G01N 31/00; G01N 15/06; G01N 53/48; G01N 1/00; G01N 37/00; G01N 33/10; B65B 1/04; B65B 3/04

(52) U.S. Cl. ........................ 422/100; 422/99; 422/102; 422/63; 422/68.1; 422/104; 436/180; 73/863.22; 73/864; 73/864.01; 73/864.11; 73/864.12; 73/864.14; 73/864.18; 73/864.21; 73/864.25; 73/864.31; 73/864.91; 141/21

(58) Field of Search ................... 422/100, 63, 68.1, 422/102, 104, 99; 436/180, 54; 73/863.32, 864, 864.01, 864.02, 864.11, 864.12, 864.14, 864.18, 864.24, 864.25, 864.31, 864.91; 141/21

(56) References Cited

U.S. PATENT DOCUMENTS 3,164,304 A    1/1965  Jager et al.
5,306,510 A  * 4/1994  Meltzer ....................... 422/100
5,439,649 A  * 8/1995  Tseung et al. .............. 118/300
5,551,487 A    9/1996  Gordon et al. .................. 141/1
5,807,522 A    9/1998  Brown et al. ................. 422/50
5,906,795 A  * 5/1999  Nakashima et al. ........ 422/100
6,063,339 A  * 5/2000  Tisone et al. ............... 422/100
6,077,713 A  * 6/2000  Dunfee et al. .................. 222/1
6,296,702 B1 * 10/2001 Bryning et al. ............. 118/401
6,372,185 B1 * 4/2002  Shumate et al. ............ 422/100

FOREIGN PATENT DOCUMENTS

WO    WO 99/36760    7/1999
WO    WO 00/54883    9/2000

OTHER PUBLICATIONS

"ArrayIt Chipmaker 2" Chipmaker Micro–Spotting Device, Online! Mar. 3, 1999, XP002153368 Retrieved from the Internet: >URL:http//www.hooked.net/telechem/biochio > retrieved on Nov. 16, 2000! –the whole document.

* cited by examiner

*Primary Examiner*—Jill Warden
*Assistant Examiner*—Brian R Gordon
(74) *Attorney, Agent, or Firm*—Armstrong, Westerman & Hattori, LLP.

(57) ABSTRACT

A present micro array manufacturing apparatus includes a substrate placement portion 11 on which a plurality of substrates can be arranged, a tighter plate 12 for storing a solution including a living body sample, a solution storing member 52 for taking in the solution from the tighter plate 12 and storing the solution therein, and a needle 51 which can be inserted into the solution storing member 52 to allow the solution stored in the solution storing member 52 to adhere onto each of the substrates by a given quantity, wherein the solution storing member 52 and needle 51 are moved in directions where they approach and part away from the substrates to thereby form spots on the substrates. And, the individual operations of the solution storing member 52 and needle 51 are carried out by single drive means 32.

10 Claims, 10 Drawing Sheets

MICRO ARRAY MANUFACTURING APPARATUS

BACKGROUND OF THE INVENTION

1. Field of the Invention

The present invention relates to a micro array manufacturing apparatus in which a large number of living body samples such as DNA fractions are arranged on substrates to thereby manufacture a living body sample micro array.

2. Description of the Related Art

At present, a technology is increasingly being developed which analyzes all genes of various living bodies efficiently. A DNA micro array is an array in which a large number of spots such as DNA fractions having a given base array are arranged on substrates such as slide glasses or silicones; and the DNA micro array is essential to the above analysis. Also, by detecting the variation of a gene using the DNA micro array, for innumerable gene-related diseases, medical treatment proper for individual patients can be performed.

In JP-Y-10-503841, there is disclosed an apparatus which is used to manufacture such micro array. In this apparatus, a test solution including DNA fractions is held in an open capillary passage formed between a pair of long and narrow members disposed spaced from each other, the leading end portions of the long and narrow members are lightly hammered at the given positions of the substrates to make the test solution to adhere onto the substrate, thereby forming solution spots on the substrates.

However, in the above-mentioned apparatus, the quantity of the test solution that can be held in the open capillary passage at a time is relatively small. Therefore, when manufacturing a large number of micro arrays at the same time, the test solution must be frequently replenished into the open capillary passage, which takes long time for manufacture of the micro arrays.

Also, in case where the quantity of the test solution is small, the test solution is easy to dry up and thus the viscosity of the test solution is easy to vary, which makes it difficult to form a large number of spots in a stable manner.

SUMMARY OF THE INVENTION

The present invention aims at eliminating the drawbacks found in the above-mentioned conventional micro array manufacturing apparatus. Accordingly, it is an object of the invention to provide a micro array manufacturing apparatus which can manufacture a micro array stably with high efficiency as well as can be manufactured at low costs.

It is another object of the invention to provide a micro array manufacturing apparatus which is able to manufacture a micro array stably with high efficiency.

In attaining the above object, according to a first aspect of the invention, there is provided a micro array manufacturing apparatus, comprising: a working table capable of arranging a plurality of substrates thereon; a solution storing portion for storing a solution including a living body sample; hold means for taking in said solution from the solution storing portion to form the spot of the solution on each of the substrates; moving means for supporting the hold means and moving it in directions where it approaches and part away from the substrates, thereby allowing the hold means to form the solution spot; and, delivery means for supporting the moving means and delivering it in an area including the working table and solution storing portion to thereby give it two-dimensional coordinates, wherein the hold means is made up of a solution storing portion for storing the solution and a needle insertable into the solution storing portion to allow the solution stored in the solution storing portion to adhere onto each of the substrates by a given quantity; the moving means includes a support portion to be delivered by the delivery means, a first movable member capable of mounting the solution storing portion thereon and mounted in such a manner that it can be moved with respect to the support portion in given directions where it approaches and parts away from the substrates, a second movable member capable of mounting the needle thereon and mounted in such a manner that it can be moved in the given directions with respect to the first movable member, and drive means for driving the second movable member; and the first movable member is driven in linking with the second movable member to be driven by the drive means.

In the first aspect of the invention, since the solution stored in the solution storing portion is allowed to adhere onto the substrate using the needle, a large quantity of solution can be stored in the solution storing portion. Even in case where spots are formed successively on a large number of substrates, there is eliminated the need to replenish the solution frequently, which makes it possible to shorten the micro array manufacturing time. Also, because a large quantity of solution can be stored in the solution storing portion, the dry-up of the solution can be restricted and variations in the viscosity of the solution can also be restricted, which makes it possible to form the spots stably for a long period of time.

Further, in the first aspect of the invention, the first movable member is driven in linking with the second movable member which is driven by the drive means. That is, the simultaneous upward and downward movement operations of the second movable member and first movable member (that is, the needle and solution storing member) as well as the upward and downward movement operation of only the second movable member (that is, the needle) after the first movable member (that is, the solution storing member) is stopped are carried out only by the single drive means. Due to this, when compared with a case in which these two operations are carried out by individual drive means, the drive source of the whole apparatus can be reduced in number and the number of parts involved with the drive source can be reduced, thereby being able to attain the reduced cost of the whole apparatus. Also, use of the single drive means can reduce the weight of the arraying head to be driven by the delivery means, which can simplify the structure the structure of the micro array manufacturing apparatus and can reduce the weight thereof. Therefore, it is possible to drive the arraying head at a high speed by the linear drive mechanisms, which makes it possible to shorten the manufacturing time of the micro array.

Also, according to a second aspect of the invention, there is provided a micro array manufacturing apparatus, comprising: a working table on which a plurality of substrates can be arranged; a solution storing portion for storing a solution including a living body sample; hold means for taking in the solution from the solution storing portion to form the spot of the solution on each of the substrates; moving means for supporting the hold means and moving it in directions where it approaches and part away from the substrates, thereby allowing the hold means to form the solution spot; and delivery means for supporting the moving means and delivering it in an area including the working table and the solution storing portion to thereby give it two-dimensional coordinates, wherein the hold means is made up of a solution storing portion for storing the solution and a needle insertable into the solution storing portion to allow the solution stored in the solution storing portion to drop down onto each of the substrates by a given quantity; and the moving means includes a base portion to be delivered by the delivery portion, a first movable member capable of mounting the solution storing portion thereon and mounted in such a manner that it can be moved with respect to the base portion in given directions where it approaches and parts away from the substrate, a first restrict member for restricting the movement of the first movable member in one direction with respect to the base portion, a second movable member capable of mounting the needle thereon and mounted in such a manner that it can be moved in the given directions with respect to the first movable member, a second restrict member for restricting the movement of the first movable member in the other direction opposite to the above-mentioned one direction with respect to the first movable member, and drive means for driving the second movable member.

In the second aspect of the invention, since the solution stored in the solution storing portion is allowed to adhere onto the substrates using the needle, a large quantity of solution can be stored and held in the solution storing portion. Even when the spots are formed successively on a large number of substrates, there is eliminated the need to replenish the solution frequently, which makes it possible to shorten the micro array manufacturing time. Also, because a large quantity of solution can be stored and held in the solution storing portion, the dry-up of the solution can be restricted and variations in the viscosity of the solution can be restricted, thereby being able to form the spots stably for a long period of time.

In the second aspect of the invention, the first movable member is driven in linking with the second movable member which is driven by the drive means. That is, the simultaneous upward and downward movement operations of the second movable member and first movable member (that is, the needle and solution storing member) as well as the upward and downward movement operation of only the second movable member (that is, the needle) after the first movable member (that is, the solution storing member) is stopped are carried out only by the single drive means. Due to this, when compared with a case in which these two operations are carried out by individual drive means, the drive source of the whole apparatus can be reduced in number and thus the number of parts involved with the drive source can be reduced, thereby being able to attain the reduced cost of the whole apparatus. Also, use of the single drive means can reduce the weight of the driven portion to be driven by the delivery means, which can simplify the structure the structure of the micro array manufacturing apparatus and can reduce the weight thereof. This can realize the high-speed driving of the driven portion by the linear drive mechanisms, so that the manufacturing time of the micro array can be shortened.

By the way, in order to facilitate the understanding of the invention, to the component elements of the micro array manufacturing apparatus of the invention, there have been added reference characters shown in the accompanying drawings while they are respectively put in parentheses. However, such expression does-not mean that the invention is limited to the illustrated embodiments of the invention.

According to a third aspect of the invention, there is provided a micro array manufacturing apparatus, comprising: a working table on which a plurality of substrates are arranged; a solution storing portion for storing a solution including a living body sample; hold means for taking in said solution from said solution storing portion to form the spot of said solution on each of said substrates; moving means for supporting said hold means and moving said hold means in directions where said hold means approaches and goes away from said substrates, thereby allowing said hold means to form said solution spot; and delivery means for supporting said moving means and delivering said moving means in an area including said working table and said solution storing portion to provide two-dimensional coordinates; wherein said hold means comprises a solution storing portion for storing said solution and a needle insertable into said solution storing portion to allow said solution stored in said solution storing portion to adhere onto each of said substrates by a given quantity.

In the third aspect of the invention, since the solution stored in the solution storing portion is allowed to adhere onto the substrate using the needle, a large quantity of solution can be stored in the solution storing portion. Even in case where spots are formed successively on a large number of substrates, there is eliminated the need to replenish the solution frequently, which makes it possible to shorten the micro array manufacturing time. Also, because a large quantity of solution can be stored in the solution storing portion, the dry-up of the solution can be restricted and variations in the viscosity of the solution can also be restricted, which makes it possible to form the spots stably for a long period of time.

According to a fourth aspect of the invention, in the micro array manufacturing apparatus of the third aspect, said solution storing portion includes a tapered interior space. In the fourth aspect of the invention, the solution storing portion includes a tapered interior space. In case where the interior space of the solution storing portion is formed in a tapered manner, the solution can be held positively and, at the same time, when the needle projects from the solution storing portion, the quantity of solution moving to the needle can be controlled properly.

According to a fifth aspect of the invention, in the micro array manufacturing apparatus of the third aspect, said needle includes a flat portion formed in said substrate side leading end portion thereof.

In the fifth aspect of the invention, in the leading end of the needle, there is formed a flat surface. Thanks to this, the deformation of the leading end portion of the needle when the leading end of the needle is contacted with the substrate can be restricted, which makes it possible to form a spot stably.

According to a sixth aspect of the invention, in the micro array manufacturing apparatus of the third aspect of the invention, said needle includes a slit for holding said solution therein.

In the sixth aspect of the invention, in the needle, there is formed a slit for holding the solution therein, which makes it possible to increase the quantity of solution that can be held.

According to a seventh aspect of the invention, in the micro array manufacturing apparatus of the third aspect of the invention, there is further provided washing means which pours a washing solution into said interior space of said solution storing portion to thereby wash said interior space of said solution storing portion.

In the seventh aspect of the invention, there is further included washing means for washing the interior space of the solution storing portion. This eliminates the possibility that the solution held by the solution storing portion in a certain step can remain within the solution storing portion until a next step. This can prevent different kinds of solutions from being mixed together.

BRIEF DESCRIPTION OF THE DRAWINGS

FIGS. 6A to 6D show the states of the solution when the needle is moved in the vertical direction with respect to the solution storing member: in particular.

FIGS. 7A and 7B show the shape of a needle disposed in the micro array manufacturing apparatus according to the first embodiment: in particular.

FIGS. 8A and 8B show a method for filling the solution into the solution storing member: in particular.

FIGS. 10A and 10B show the shape of a needle employed in a micro array manufacturing apparatus according to a second embodiment: in particular.

DETAILED DESCRIPTION OF THE PREFERRED EMBODIMENTS

Hereinafter, a description will be given in more detail of preferred embodiments of the invention with reference to the accompanying drawings.

(First Embodiment)

A first embodiment of a micro array manufacturing apparatus according to the invention will be described with reference to FIGS. 1–8.

Figure 1:
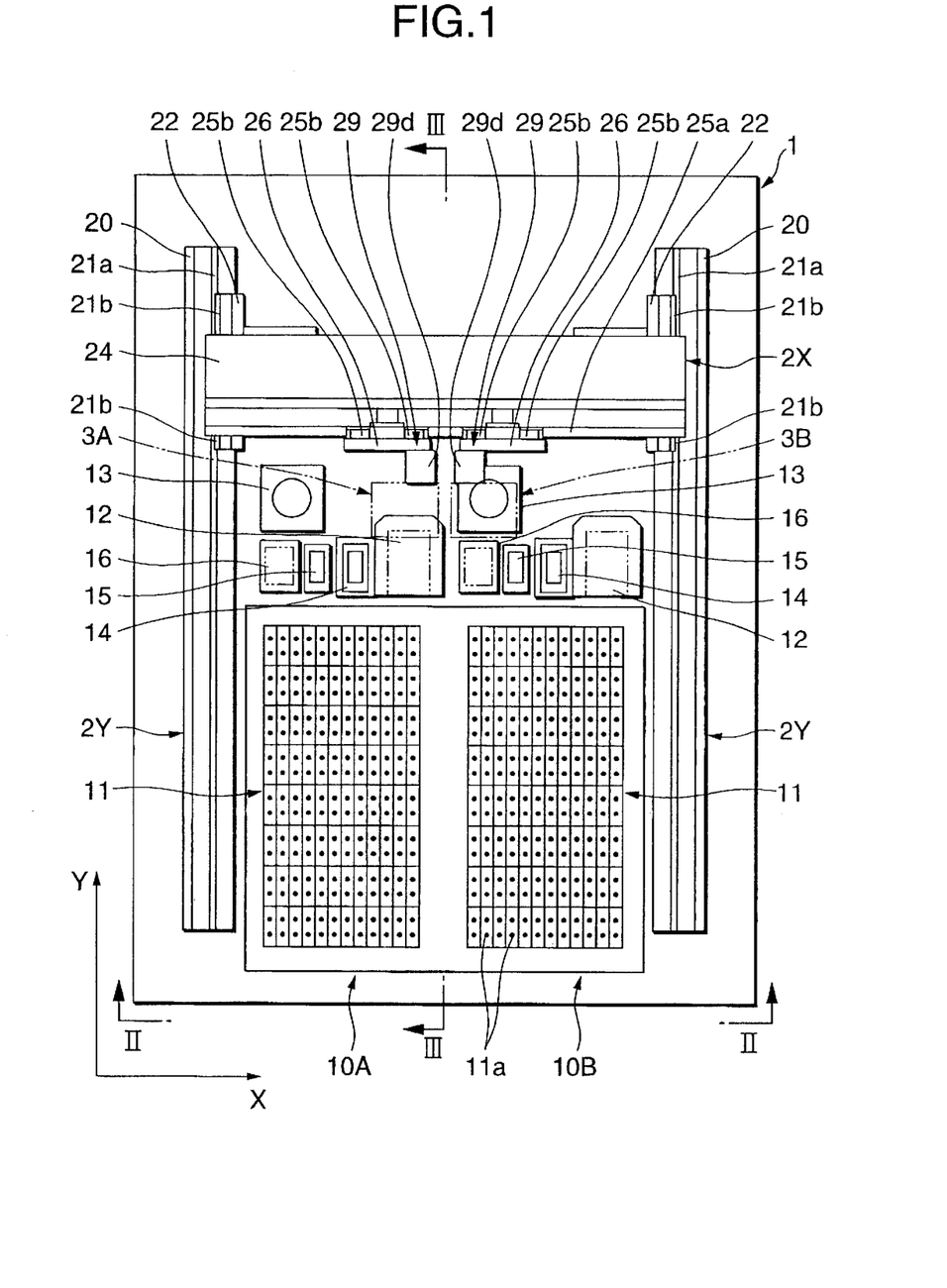
FIG. 1 is a plan view of a micro array manufacturing apparatus according to a first embodiment of the invention.
Figure 2:
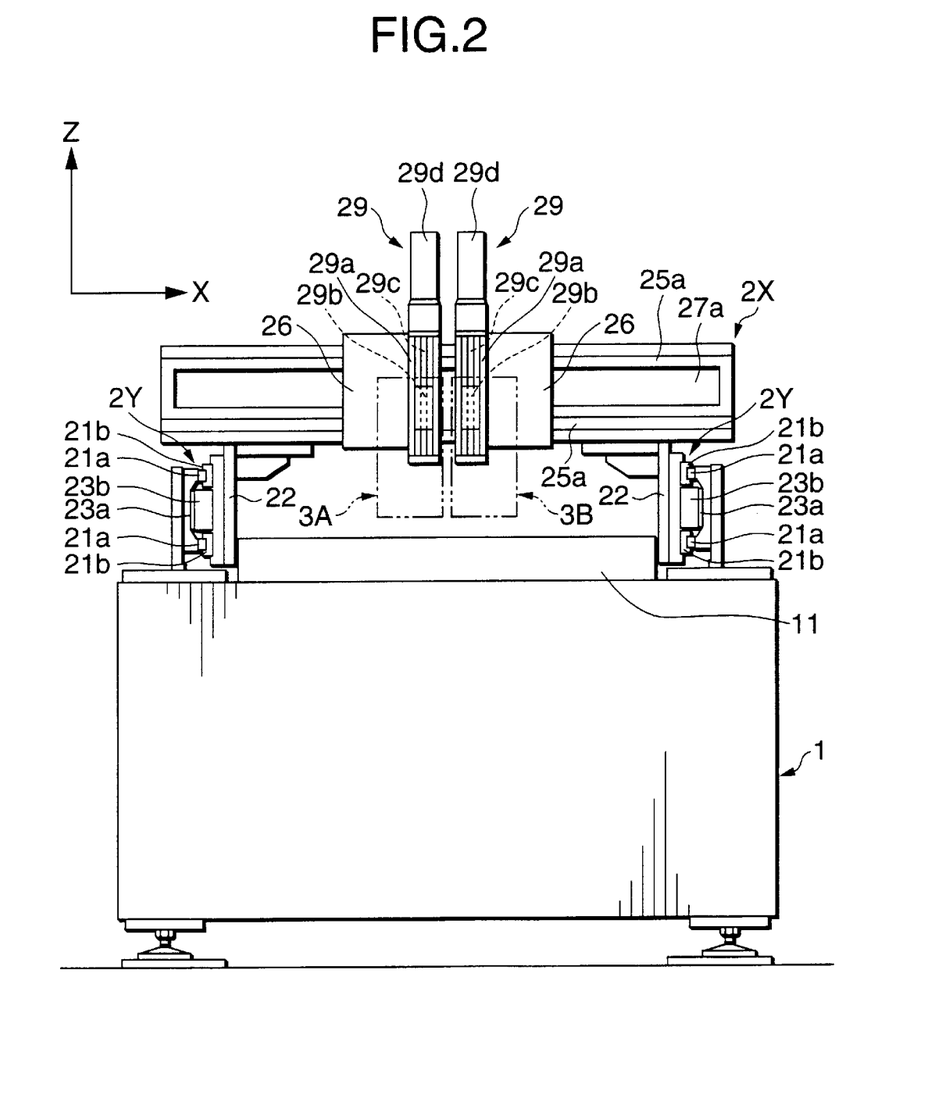
FIG. 2 is a front view of the micro array manufacturing apparatus according to the first embodiment, when it is viewed from the direction of the line II—II shown in FIG. 1.

FIG. 1 is a plan view of a micro array manufacturing apparatus according to the first embodiment of the invention; FIG. 2 is a front view of the present micro array manufacturing apparatus, when it is viewed from the direction of the line II—II shown in FIG. 1; and, FIG. 3 is a section view of the present micro array manufacturing apparatus, when it is viewed from the direction of the line III—III shown in FIG. 1.

Figure 3:
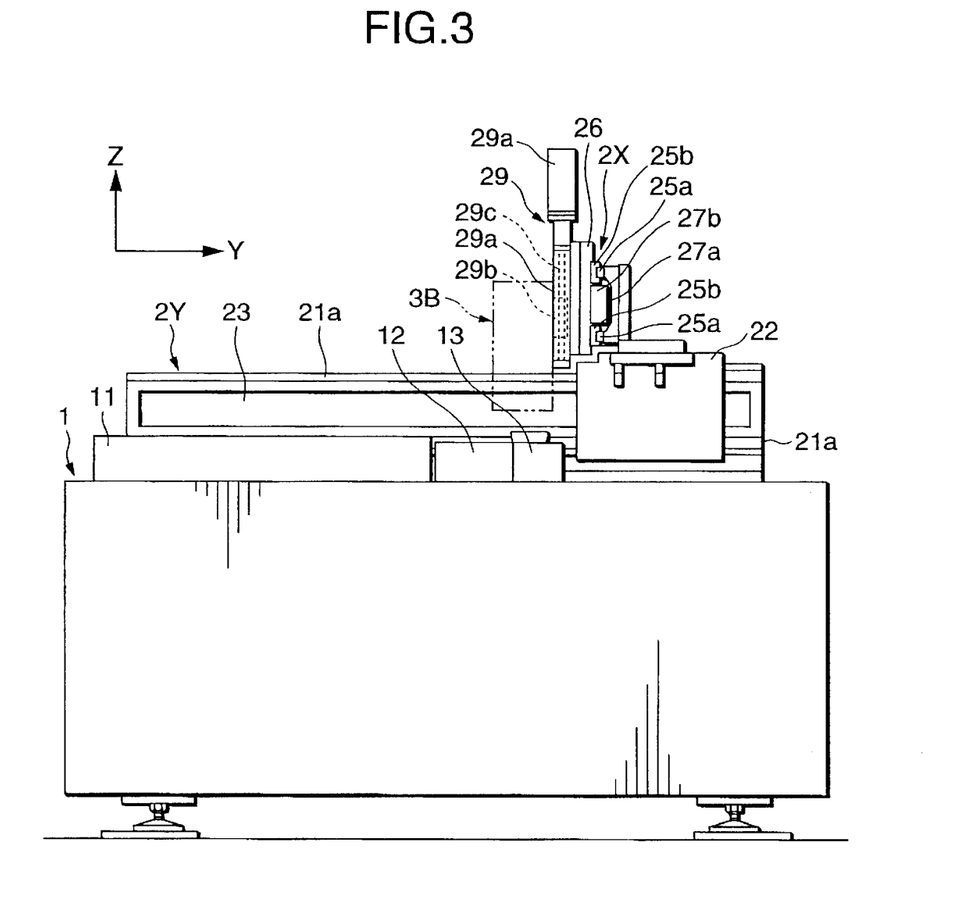
FIG. 3 is a section view of the micro array manufacturing apparatus according to the first embodiment, when it is viewed from the direction of the line III—III shown in FIG. 1.

As shown in FIGS. 1 to 3, according to first embodiment, the micro array manufacturing apparatus comprises a base body 1 for carrying thereon a large number of (in FIG. 1, 192 sheets of) substrates on which a micro array is produced, a pair of arraying heads 3A, 3B respectively mounted on the base body 1, a pair of linear drive mechanisms 2Y for driving the arraying heads 3A, 3B in the Y-axis direction (in FIG. 1, in the vertical direction) at the same time, and a linear drive mechanism 2x for driving the arraying heads 3A, 3B in the X-axis direction (in FIG. 1, in the right and left direction). By the way, when the arraying heads 3A, 3B may not be specifically distinguished from each other, they will be expressed below simply as an arraying head 3. The details of the arraying head 3 will be described later.

The upper surface of the base body 1 is divided into two blocks 10A, 10B which are arranged side by side in the left and right direction in FIG. 1 and, in the two blocks 10A, 10B, there are disposed the same elements respectively. The two blocks 10A, 10B respectively correspond to the moving ranges of the arraying heads 3A, 3B within the XY plane.

As shown in FIG. 1, in each of the two blocks 10A, 10B, there is disposed a substrate placement portion 11 serving as an operation table on which there are placed a large number of substrates in a matrix manner, a tighter plate 12 serving as a solution storing portion in which there are arranged a large number of recessed portions for storing a solution including DNA fractions, an ultrasonic washer 13 for washing a solution storing member (which will be described later) included in the arraying head 3 from the outside thereof using water with an ultrasonic wave applied thereto, a rinsing portion 14 for rinsing the solution storing member, a drying portion 15 for drying the washed and rinsed storing member, and a test table 16 on which two substrates or dummy substrates for producing a micro array experimentally are placed.

In the substrate placement portion 11, there are opened up suction holes 11a (FIG. 1) so as to correspond to the substrate, while the pipe passages of a vacuum apparatus (not shown) are connected to the suction holes 11a. In case where the vacuum apparatus is operated, the air is sucked from the suction holes 11a to thereby be able to fix the substrates to the substrate placement portion 11.

The pair of linear drive mechanisms 2Y each comprises a longitudinally fixed frame 20 extended in the Y-axis direction, a linear guide made up of a rail 21a mounted on the fixed frame 20 so as to extend in the Y-axis direction and a slider 21b movably assembled to the rail 21a, a table 22 to be guided by the linear guide, and a linear motor for driving the table 22. The linear motor comprises a magnet 23a serving as a secondary side of the motor extending in the Y-axis direction and a coil 23b serving as a primary side of the motor mounted on the back side of the table 22 so as to be opposed to the magnet 23a.

Also, the linear drive mechanism 2X comprises a longitudinally movable frame 24 interposed between the pair of tables 22 to be driven by the two linear drive mechanisms 2Y so as to be bridge over the two tables 22 in the X-axis direction, a linear guide made up of a rail 25a mounted on the movable frame 24 so as to extend in the X-axis direction and two sliders 25b respectively movably assembled to the rail 25a, a table 26 to be guided by the linear guide, and a linear motor for driving the table 26. The linear motor is made up of a magnet serving as a secondary side of the motor extending in the X-axis direction and a coil 27b serving as a primary side of the motor mounted on the back surface of the table 26 so as to be opposed to the magnet 27a.

On the table 26, there are mounted two electric actuators 29. In detail, each of the electric actuators 29 includes a rail 29a having a U-shaped section and a slider 29b incorporated into the rail 29a so as to be free to reciprocate. And, in the slider 29b, there is disposed a nut (not shown); and, in the electric actuator 29, there is disposed a screw shaft 29 which can be threadedly engaged with the nut, and there is also disposed a motor 29d for driving or rotating the screw shaft 29c.

The arraying head 3 is mounted on the slider 29b of the electric actuator 29. The operation direction of the electric actuator 29 is the vertical direction (Z-axial direction) that is perpendicular not only to X-axial direction but also to the Y-axial direction. That is, the electric actuator 29 operates as part of moving means for moving hold means (which will be discussed later) included in the arraying head 3 in directions where the hold means approaches or parts away from the substrates placed on the substrate placement portion 11.

Also, the two linear drive mechanisms 2Y and linear drive mechanism 2X operate as delivery means which supports the electric actuator 29 (and thus the arraying head 3) and delivers the same in an area including the substrate placement portion 11 and tighter plate 12 to thereby give two-dimensional coordinates to the electric actuator 29.

Figure 4:
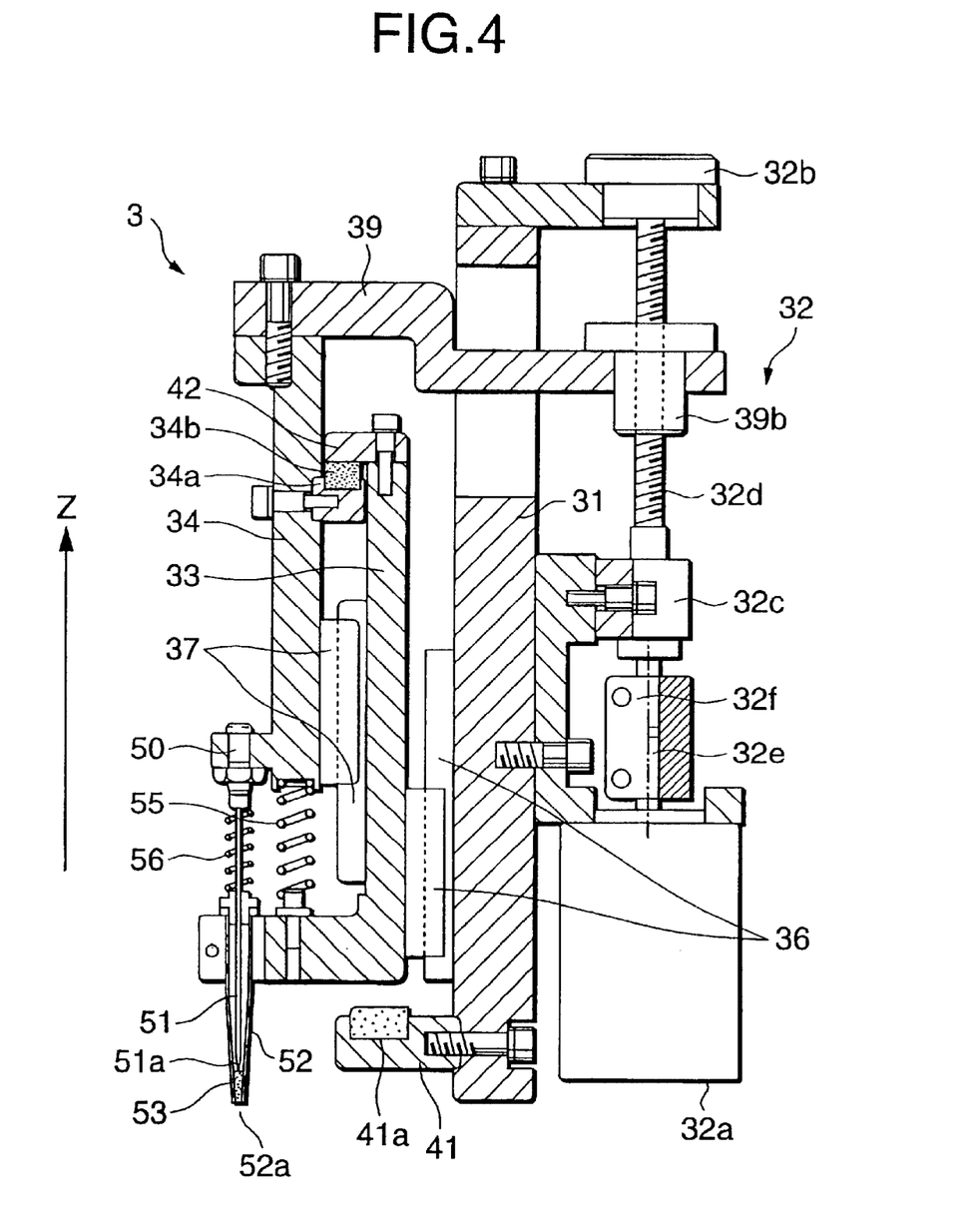
FIG. 4 is a section view of the structure of an arraying head disposed in the micro array manufacturing apparatus according to the first embodiment.

Now, FIG. 4 is a section view of the arraying head 3, showing the structure thereof. As shown in FIG. 4, the arraying head 3 comprises a support portion 31 which is mounted on the table 26 (not shown in FIG. 4) and is delivered, drive means 32 including a servo motor 32a mounted on the support portion 31, a first movable member 33 mounted freely movable through a linear guide 36 made up of a rail and a slider in the vertical direction (Z-axis direction) in FIG. 4, that is, in a direction where the first movable member 33 approaches and parts away from the substrates placed on the substrate placement portion 11, and a second movable member 34 mounted freely movable through a linear guide 37 made up of a rail and a slider in the vertical direction with respect to the first movable member 33. Also, between the first and second movable member 33, 34, there are interposed compression springs 55, 56.

As described above, the support portion 31 is mounted on the table 26 and, by operating the motor 29d shown in FIGS. 1 to 3, the support portion 31 can be moved in the vertical direction. Due to this, the position of the whole arraying head 3 in the vertical direction (Z-axis direction) can be adjusted to the thicknesses of the substrates.

The second movable member 34 can be driven by the drive means 32. The drive means 32 is structured in the following manner and also includes the above-mentioned servo motor 32a.

That is, as shown in FIG. 4, the drive means 32 comprises a screw shaft 32d rotatably mounted on the support portion 31 of the arraying head 3 at the two end portions thereof through bearings 32b, 32c, a coupler 32f for coupling the screw shaft 32d with the output shaft 32e of the servo motor 32a, and a nut 39b mounted through a connecting arm 39a on the upper end portion of the second movable member 34 to be threadedly engageable with the screw shaft 32d. By the way, between the screw shaft 32d and nut 39b, there are interposed a large number of balls (not shown) and, in the nut 39b, there is formed an endless circulation passage through which the balls circulate; that is, the balls are allowed to circulate through the endless circulation passage due to the relative rotation between the screw shaft 32b and nut 39b.

Figure 5:
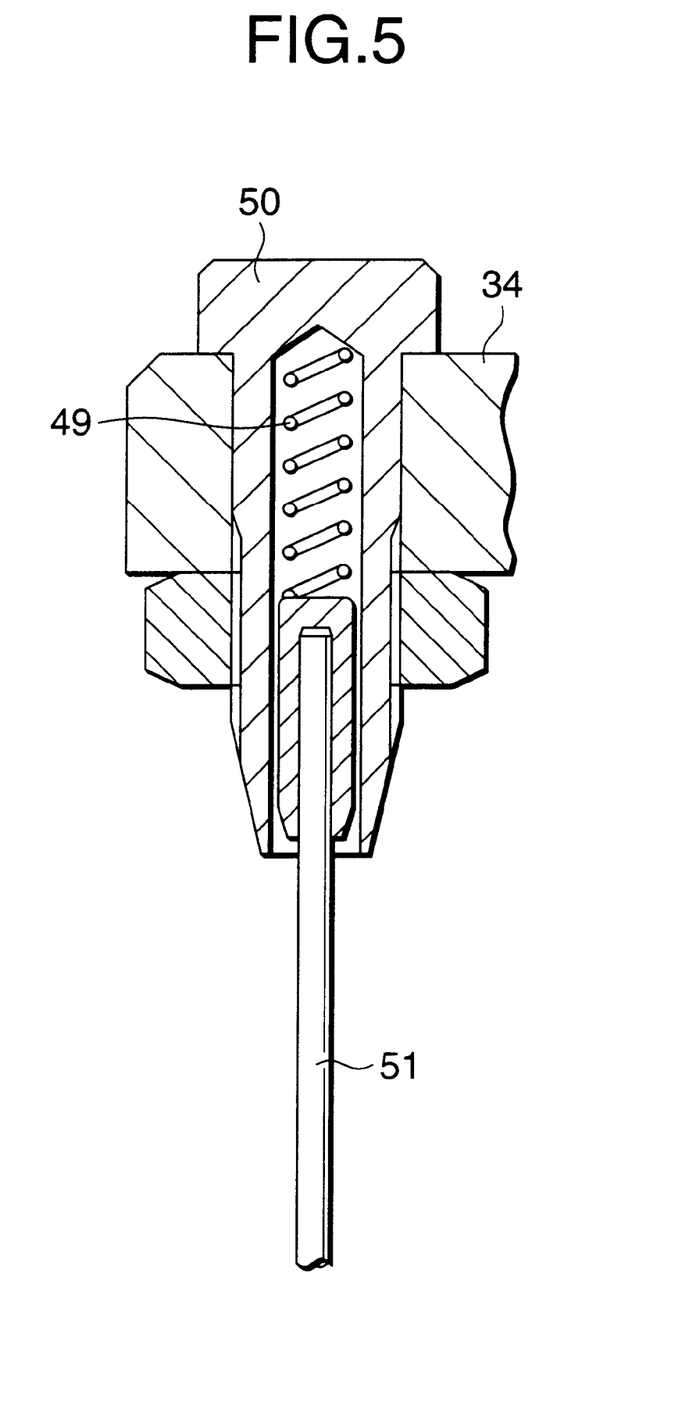
FIG. 5 is an enlarged view of the needle mounting portion of the arraying head shown in FIG. 4.

On the lower end portion of the second movable member 34, there is mounted a needle 51 in such a manner that the leading end of the needle 51 can be contacted with the substrates placed on the substrate placement portion 11. The needle 51 is mounted in the vertical direction with respect to the second movable member 34. Specifically, as shown in FIG. 5, there is used a mounting member 50 which is used to mount the needle 51 onto the second movable member 34; and, the mounting member 50 is formed hollow and thus the upper end portion of the needle 51 is inserted into the hollow interior space of the mounting member 50. And, in the interior space, there is disposed a coiled spring 49 so as to be able to receive the upper end of the needle 51. When the needle 51 moves down together with the second movable member 34 and the leading end thereof is contacted with the substrates, the coiled spring 49 is compressed to thereby buffer the contact operation. Also, while the second movable member 34 continues to move down even after the needle 51 is contacted with the substrate, the coiled spring 49 is compressed by an amount corresponding to the amount of the downward movement of the second movable member 34. This gives a given contact force to the needle 51.

On the lower end portion of the first movable member 33, there is mounted a solution storing member 52 serving as a solution storing portion for storing therein a solution 53 to be supplied to the substrates. As shown in FIGS. 4 and 6, the solution storing member 52 is formed in a tapered pipe shape; and, into the tapered interior space of the solution storing member 52, there is stored the needle 51 together with the solution 53. Also, the leading end portion 51a of the needle 51 can be projected from and retreated into an opening 52a which is formed in the lower end of the solution storing member 52.

In case where the needle 51 projects from the solution storing member 52, it carries out the solution 53 within the solution storing member 52 by a given quantity and allows the given quantity of solution to adhere to the substrate placed on the substrate placement portion 11.

The solution storing member 52 and needle 51 are generically called hold means. The hold means takes in the solution from the tighter plate 12 serving as a solution storing portion and holds the solution therein. The hold means is used to form the spot of the solution 53 on the substrate placed on the substrate placement portion 11.

By the way, of the component members of the arraying head 3, the component members except for the hold means (the solution storing member 52 and needle 51) and the previously described electric actuator 29 are generically referred to as moving means. The moving means supports the hold means and moves it in a direction where it approaches and parts away from the substrates placed on the substrate placement portion 11, thereby allowing the hold means to form the above-mentioned spot.

As shown in FIG. 4, in the lower end portion of the support portion 31, there is disposed a first restrict member 41 including a damper 41a; and, the lower end of the first movable member 33 can be contacted with the first restrict member 41. The first restrict member 41 restricts the movement of the first movable member 33 with respect to the support portion 31 in the downward direction (which is the opposite direction to the arrow mark Z direction shown in FIG. 4) at a given position.

Also, on the upper end portion of the first movable member 33, there is disposed a second restrict member 42;

and, a contact pin 34a, which is provided on and projected from the neighboring portion of the upper end of the second movable member 34, can be contacted with the second restrict member 42. The second restrict member 42 restricts the movement of the second movable member 34 with respect to the first movable member in the upward direction (that is, the arrow mark Z direction shown in FIG. 4) at a given position. By the way, the contact pin 34a includes a damper 34b.

As shown in FIGS. 4 to 7, the leading end portion 51a of the needle 51 is formed in a tapered shape. Also, as shown in FIGS. 7A and 7B, in the leading end portion 51a, there is formed a circular-shaped flat surface 51b.

In case where the servo motor 32a is operated, the screw shaft 32d is rotated and the nut 39b reciprocates between the upper and lower positions, whereby the second movable member 34 is driven or reciprocated between the upper and lower positions. FIG. 4 shows a state in which the second movable member 34 is situated between the upper and lower positions.

When the second movable member 34 is situated at the upper position, the contact pin 34a disposed on the second movable member 34 is contacted with the second restrict member 42 disposed on the first movable member 33 and the lower end surface of the first movable member 33 is spaced apart from the first movable member 33 disposed on the support portion 31. At the then time, the relative position relation between the first and second movable members 33 and 34 is similar to that shown in FIG. 4, and the two movable members 33 and 34 are moved more upwardly than they are shown in FIG. 4.

On the other hand, when the second movable member 34 is situated at the lower position, the lower end surface of the first movable member 33 is contacted with the first restrict member 41 disposed on the support portion 31. Also, the contact pin 34a disposed on the second movable member 34 is separated from the second restrict member 42 disposed on the first movable member 33, so that the compression springs 55, 56 are compressed.

When the second movable member 34 is driven from the upper position toward the lower position, until the lower end face of the first movable member 33 is contacted with the first restrict member 41, the second movable member 34 moves down together with the first movable member 33 while it remains in contact with the second restrict member 42 through the contact pin 34a. In case where the lower end face of the first movable member 33 is contacted with the first restrict member 41, the first movable member 33 stays at the then position. After then, only the second movable member 34 moves down to reach the lower position.

When the second movable member 34 is driven from the lower position toward the upper position, until the contact pin 34a disposed on the second movable member 34 is contacted with the second restrict member 42, only the second movable member 34 moves up, whereas the first movable member 33 stays while it is in contact with the first restrict member 41. In case where the contact pin 34a is contacted with the second restrict member 42, the second movable member 34 moves up together with the first movable member 33 and thus the lower end face of the first movable member 33 is separated from the first restrict member 41.

Now, FIGS. 6A to 6D are respectively section views of the solution storing member 52, showing the states of the solution when the needle 51 moves in the vertical direction with respect to the solution storing member.

Figure 6A:
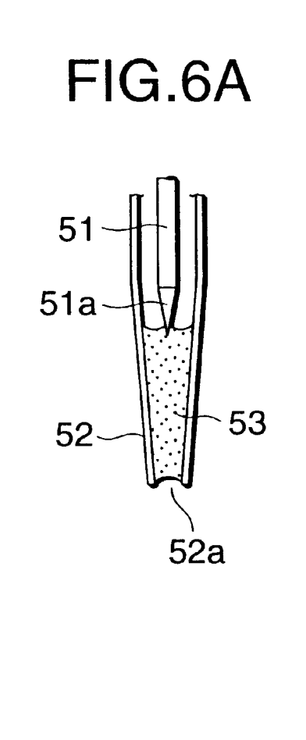
FIG. 6A is a section view of a state in which the needle is completely stored in the solution storing member.
Figure 6B:
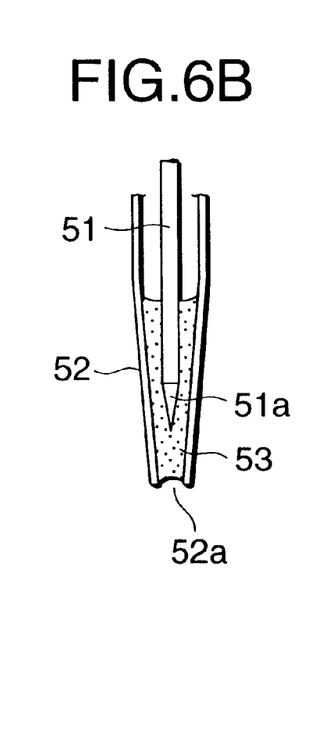
FIG. 6B is a section view of a state in which the needle is situated downwardly of the position thereof shown in FIG. 6A.
Figure 6C:
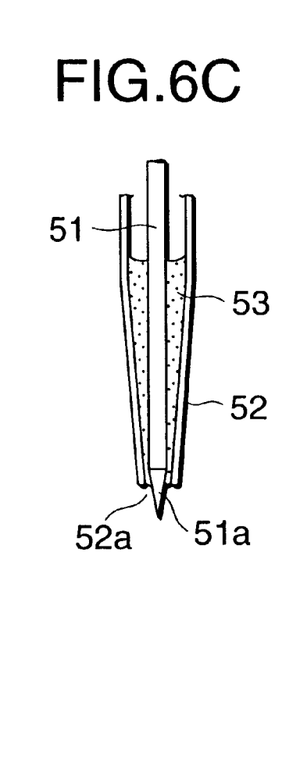
FIG. 6C is a section view of a state in which the leading end of the needle is projected from the leading end of the solution storing member; and, FIG. 6D is a section view of a state in which the leading end of the needle is contacted with the leading end of a substrate.
Figure 6D:
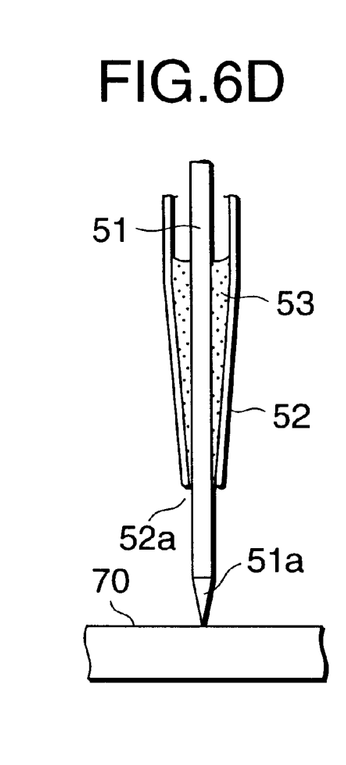

When the second movable member 34 is situated at the upper position, as shown in FIG. 6A, the needle 51 is completely stored in the interior portion of the solution storing member 52. In case where the second movable member 34 is driven from the upper position toward the lower position, until the lower end of the first movable member 33 is contacted with the first restrict member 41, the needle 51 and solution storing member 52 move down while maintaining the position relation shown in FIG. 6A. In case where the lower end of the first movable member 33 is contacted with the first restrict member 41, as shown in FIGS. 6B and 6C sequentially in this order, only the needle 51 continues to move down. As shown in FIG. 6C, when the leading end 51a of the needle 51 is projected from the opening 52a of the solution storing member 52, the solution adheres to the surface of the needle 51. And, as shown in FIG. 6D, in case where the leading end of the needle 51 is contacted with the substrate 70, the solution adhering to the leading end of the needle 51 moves and adheres to the substrate 70 as a fine solution drop, thereby forming a spot.

As can be seen clearly from the foregoing description, in the first embodiment, the first movable member 33 is driven in linking with the second movable member 34 which can be driven by the drive means 32. That is, the simultaneous upward and downward movement operation of the second movable member 34 and first movable member 33 (that is, the needle 51 and solution storing member 52) as well as the upward and downward movement operation of only the second movable member 34 (that is, the needle 51) after the first movable member (that is, the solution storing member 52) is stopped are carried out only by the single drive means 32 including the servo motor 32a. Due to this, when compared with a case in which these two operations are carried out by individual drive means, the drive source of the whole apparatus can be reduced in number and the number of parts involved with the drive source can be reduced, thereby being able to attain the reduced cost of the whole apparatus. Also, use of the single drive means can reduce the weight of the arraying head 3 including the present drive means, which makes it possible to simplify the structure of the micro array manufacturing apparatus and reduce the weight thereof. Therefore, it is possible to drive the arraying head 3 at a high speed by the linear drive mechanism 2X and 2Y, which makes it possible to shorten the manufacturing time of the micro array.

Figure 7A:
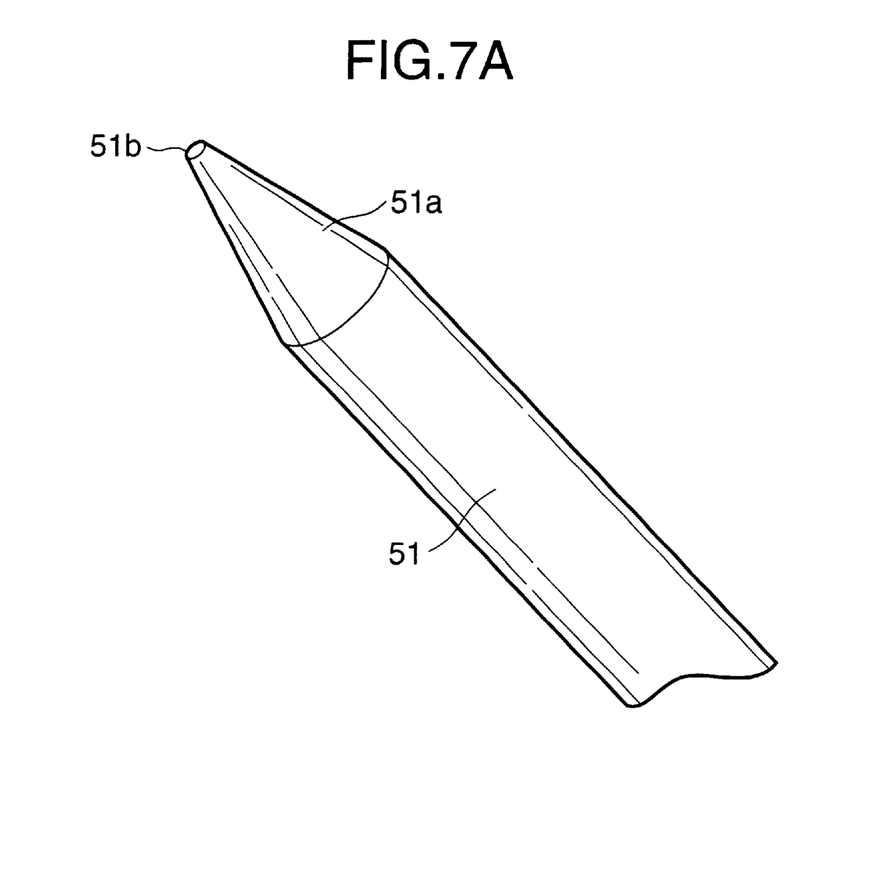
FIG. 7A is a perspective view of the needle; and, FIG. 7B is a plan view of the leading end portion of the needle when it is viewed from the axial direction of the needle.
Figure 7B:
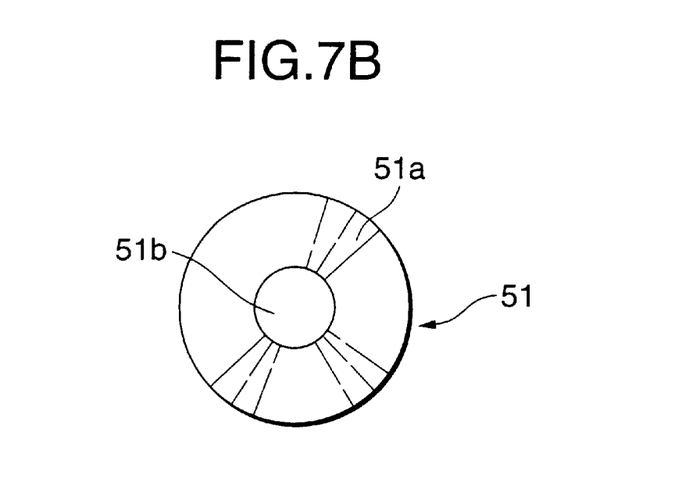

As shown in FIGS. 7A and 7B, in the present embodiment, in the leading end of the needle 51, there is formed a circular-shaped flat surface 51b. Thanks to this, even in case where the spots are formed repeatedly, the deformation of the leading end of the needle 51 can be minimized. Therefore, a large number of spots can be formed successively and stably with no frequent replacement of the needle 51.

By the way, the leading end of the needle 51 may not be always formed in a plane but it may also be formed in a curved surface. In brief, the leading end of the needle 51 may have a shape which can restrict the deformation thereof. Also, the shape of the flat surface 51b, when it is viewed from above the axial line of the needle 51, may not be a circular shape but, for example, it may be a rectangular shape. However, when fine spots are arrayed with a small pitch, preferably, there may be employed a shape near to a circle because the diameters of the spots can be stabilized.

Next, description will be given below of a method for filling the solution into the solution storing member 52 with reference to FIGS. 8A and 8B.

Figure 8A:
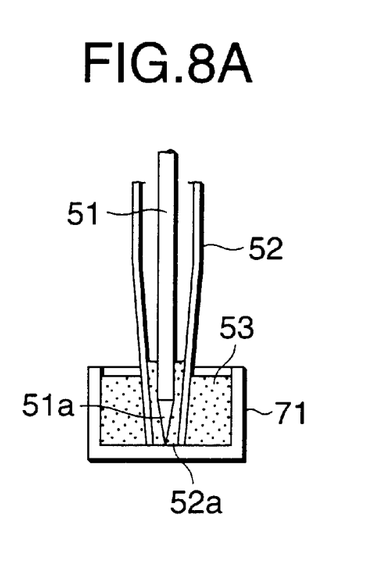
FIG. 8A is a section view of a state just after the leading end of the solution storing member is immersed in the solution; and, FIG. 8B is a section view of a state in which the solution is filled into the solution storing member due to capillary action.
Figure 8B:
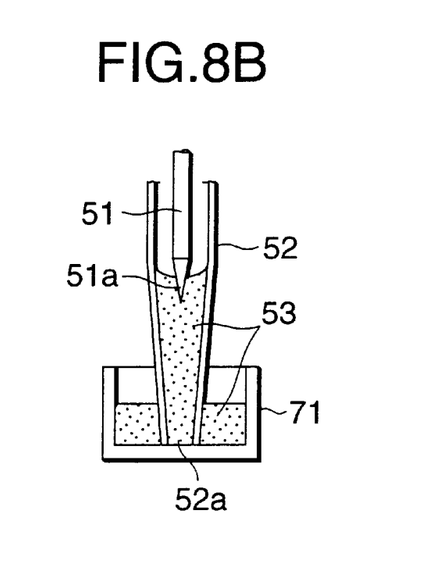

At first, as shown in FIG. 8A, the solution storing member 52 is inserted into a given recessed portion 71 which is formed in the interior portion of the tighter plate 12, so that the leading end of the solution storing member 52 is immersed in the solution 53. At the then time, the leading end of the needle 51 is set at a position just before it projects from the opening 52a of the solution storing member 52. In case where the leading end of the solution storing member 52 is immersed in the solution 53 in this manner, the solution within the recessed portion 71 is pulled into the interior portion of the solution storing member 52 due to capillary action so that the solution storing member 52 is filled with the solution to a certain degree. Next, in case where the needle 51 is moved upward while the solution storing member 52 remains fixed, due to the adhering force of the solution with respect to the leading end of the needle 51, the liquid surface of the solution is raised in accordance with the upward movement of the needle 51, so that a large quantity of solution is filled into the solution storing member 52. In case where the solution storing member 52 and needle 51 are pulled up from this state, the solution 53 filled into the solution storing member 52 is held as it is within the solution storing member 52.

As described above, according to the present embodiment, since the solution 52 is filled into the interior portion of the solution storing member 52, a relatively large quantity of solution 53 can be stored in the solution storing member 52. Thanks to this, even in case where spots are successively formed on a large number of substrates, there is eliminated the need to replenish the solution 53 frequently, which makes it possible to reduce the manufacturing time of the micro array. Also, since a large quantity of solution 53 can be stored and held in the solution storing member 52, the dry-up of the solution 53 can be restricted, thereby being able to restrict variations in the viscosity of the solution. Accordingly, not only the spots can be formed stably for a long period of time but also the yield rate of the micro array can be enhanced. Especially, the solution is normally easy to dry up when the solution is carried at a high speed; however, according to the present embodiment, even when the solution is carried at a high speed, the state and viscosity of the solution 53 can be held in a stable manner for a long period of time.

Also, according to the present embodiment, the interior space of the solution storing member 52 is formed in a tapered shape. Due to this, the solution 53 can be held positively and, at the same time, when the needle 51 projects from the solution storing member 52, the quantity of solution moving to the needle 51 can be controlled properly.

Figure 9:
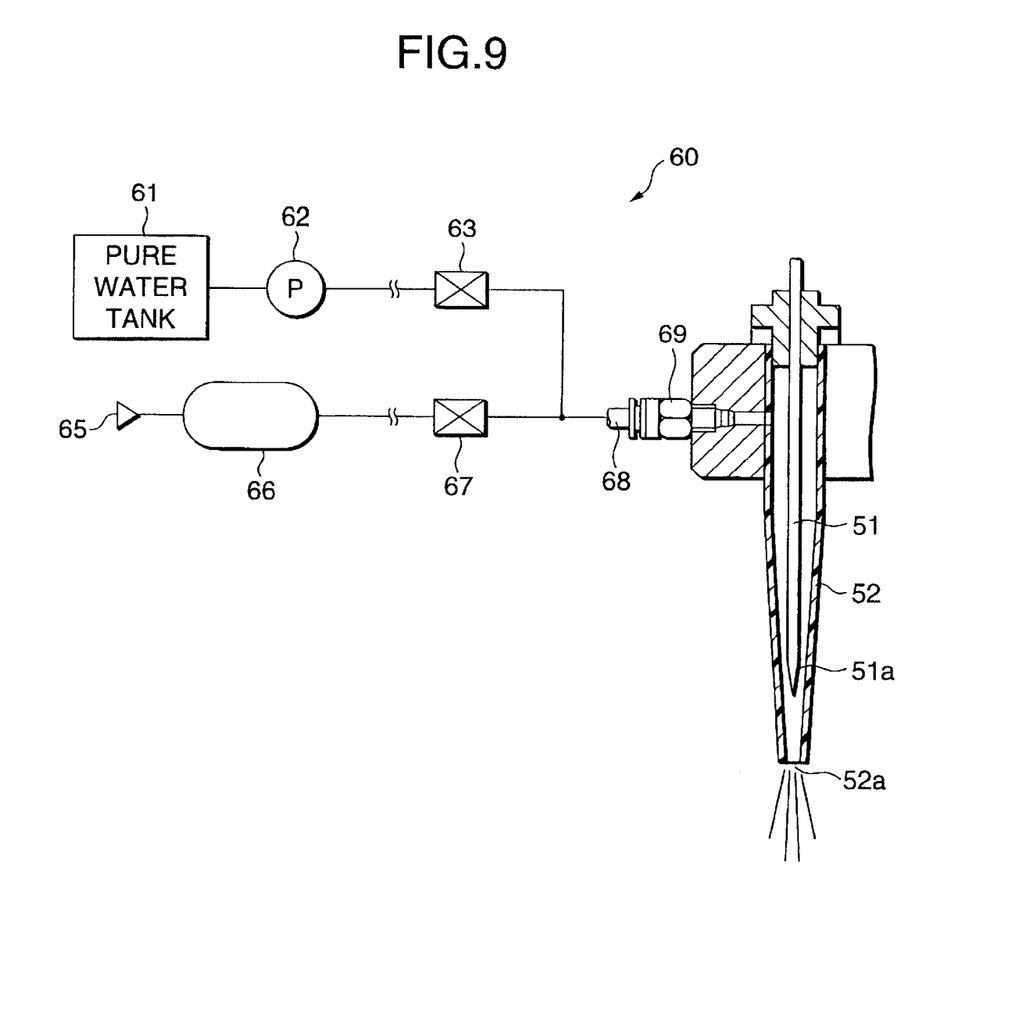
FIG. 9 shows washing means for washing the interior portion of the solution storing member using the flow of water.

Now, FIG. 9 shows washing means which is used to wash the interior space of the solution storing member 52. This washing means 60 comprises a pure water tank 61 for storing superpure water as washing solution, a pump 62 for supplying the superpure water from the pure water tank 61, an electromagnetic valve 63 for adjusting the supply quantity of the superpure water, an air pressure source 65 for producing compressed air, a tank 66 for reducing the pulsation of the air pressure formed by the air pressure source 65, an electromagnetic valve 67 for adjusting the quantity of the air supplied from the tank 66, a flexible pipe 68 for feeding the superpure water supplied through the electromagnetic valve 63 and the air supplied through the electromagnetic valve 67, and a plug 69 mounted on the solution storing member 52. As shown in FIG. 9, to the plug 69, there is connected the flexible pipe 68.

Since the superpure water can be poured into the interior space of the solution storing member 52 through the plug 69 by using the washing means shown in FIG. 9, the interior portion of the solution storing member 52 hard to be washed by the ultrasonic washing machine 13 can be washed sufficiently. The water that is left in the interior portion of the solution storing member 52 can be discharged by the compressed air.

Due to the fact that the interior portion of the solution storing member 52 is washed in this manner, there is eliminated the possibility that the solution held in a certain step by the solution storing member 52 can reside in the interior portion of the solution storing member 52 until a next step. Also, the exterior portion of the solution storing member 52 is sufficiently washed by the ultrasonic washing machine 13 and rinsing machine 14, which eliminates the possibility that the solution used in a certain step can adhere to the exterior portion of the solution storing member 52 until a next step. This can prevent different kinds of solutions from being mixed together.

By the way, when the solution storing member 52 is washed by the washing means 60, the solution storing member 52 should be positioned in the rinsing portion 14.

Next, description will be given below of the operation of a micro array manufacturing apparatus according to the embodiment under the procedure for manufacturing the micro array. By the way, in the following steps, the linear drive mechanism 2X, linear drive mechanisms 2Y and electric actuator 29 are operated properly to thereby position the arraying head 3 at given positions sequentially. This controlling operation is carried out by a control unit (not shown).

To manufacture the micro array, at first, in a state where the arraying head 3 is retreated from the substrate placement portion 11, a plurality of (for example, 96 sheets of) substrates are arranged on the substrate placement portions 11 of the blocks 10A, 10B, and the previously described vacuum apparatus is operated to thereby suck and fix the substrates. In the respective recessed portions of the tighter plate 12, for example, there are inserted a plurality of solutions which respectively contain DNA fractions different from one another. A substrate for forming a micro array experimentally or a dummy substrate is fixed onto the test table 16. In the test table 16, similarly to the substrate placement portion 11, there are formed suction holes (not shown) for sucking the substrates; and, the substrates on the test table 16, similarly to the substrate placement portion 11, are sucked and fixed by the vacuum apparatus.

Next, the spot of the solution is experimentally formed on the substrate of the test table 16 to thereby adjust the apparatus and the viscosity of the solution viscosity. The experimental spot forming step includes a step shown in FIGS. 8A and 8B to fill the solution and a step shown in FIGS. 6A to 6D to form the spot. Also, as the need arises, the experimental spot forming step may further include a step (which will be discussed later) to wash and dry the solution storing member 52.

By adjusting the viscosities of the respective solutions in the above-mentioned manner, the spot diameters of the respective solutions can be optimized.

After completion of the above-mentioned adjustment operation, spots are formed on the substrates respectively fixed to the substrate placement portion 11. At first, the first kind of solution is filled into the solution storing member 52 according to the step shown in FIGS. 8A and 8B and spots are sequentially formed on all of the substrates fixed to the substrate placement portion 11 according to the step shown in FIGS. 6A to 6D. In order to prevent the solution of the solution storing member 52 from running short, during formation of the spots, the solution may be replenished to the solution storing member 52 as the need arises. In case where the formation of spots on the all substrates using the first kind of solution is completed, the solution residing in the interior portion of the solution storing member 52 is washed and dried by the washing means 60 shown in FIG. 9 and, at the same time, the exterior portion of the solution storing member 52 is washed by the ultrasonic washing machine 13 and rinsing machine 14. Further, in the drying portion 15, the exterior portion of the solution storing member 52 is dried up.

Next, spots are formed on the all substrates using the second kind of solution and then the solution storing member 52 is washed according a similar method. These steps are repeated for all kinds of solutions to thereby carry out spot formation for all kinds of solutions, whereby micro arrays are manufactured on all substrates.

By the way, according to the present embodiment, the leading end portion of the needle is formed in a tapered shape. However, the shape of the needle is not limited to this but the needle may have any other shapes. Also, although the solution storing member 52 is formed in a tapered shape according to the present embodiment, the shape of the solution storing member 52 may be selected arbitrarily.

(Second Embodiment)

Figure 10A:
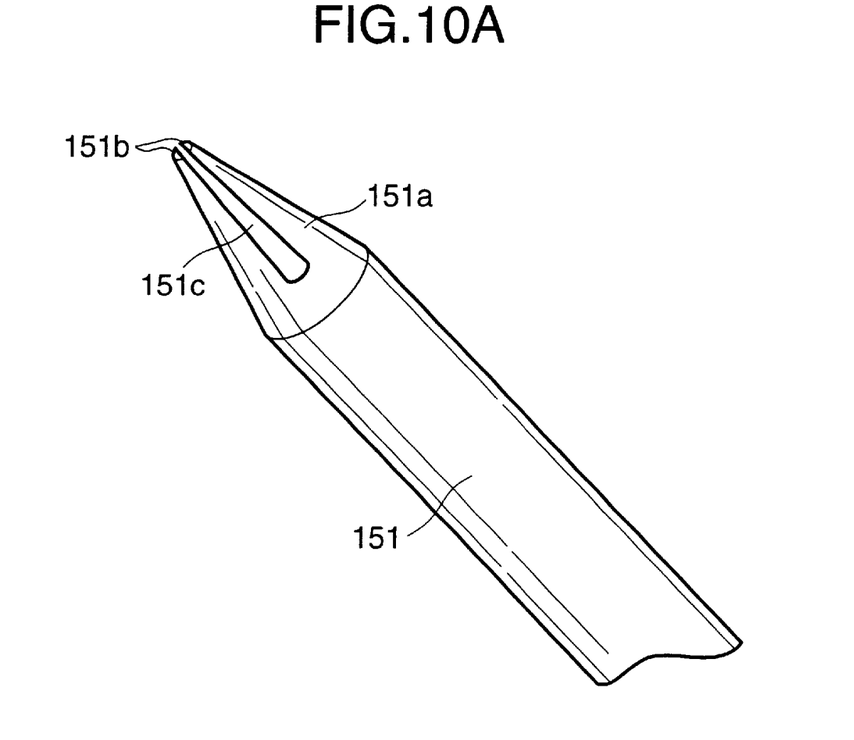
FIG. 10A is a perspective view of the needle; and, FIG. 10B is a plan view of the leading end portion of the needle when it is viewed from the axial direction of the needle.
Figure 10B:
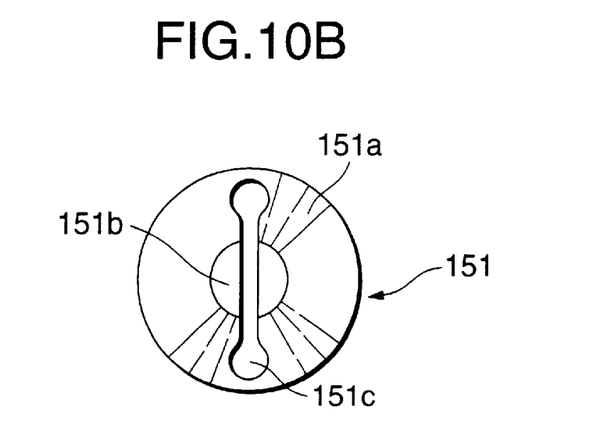

Now, description will be given below of a second embodiment of a micro array manufacturing apparatus according to the invention with reference to FIGS. 10A and 10B. By the way, in the second embodiment, there is omitted the description of the same components thereof as those in the previously described first embodiment.

In the second embodiment, in the leading end portion of the needle, there is formed a slit. As shown in FIGS. 10A and FIG. 10B, the leading end portion 151a of the needle 151 is formed in a tapered shape. Also, in the leading end portion 151a, there are formed a circular-shaped flat surface 151b for restricting the deformation of the needle leading end portion and a slit 151c extending along the axial direction of the needle 151. The slit 151c is opened in such a manner that it crosses the center of the flat surface 151b.

In case where the slit 151c is formed in this manner, the solution can be held in the interior portion of the slit 151c, thereby being able to increase the quantity of solution which can be held in the needle 151. Therefore, formation of such slit is suitable in a case where a spot having a relatively large diameter is to be formed.

As has been described heretofore, in the micro array manufacturing apparatus according to the invention, there are disposed a solution storing portion for storing a solution therein and a needle which projects into the solution storing portion to allow the solution stored in the solution storing portion to adhere onto each substrate by a given quantity. Since the solution storing portion is capable of storing a large quantity of solution, even in case where spots are formed successively on a large number of substrates, it is not necessary to replenish the solution frequently, which makes it possible to reduce the manufacturing time of the micro array. Also, because a large quantity of solution can be stored in the solution storing portion, the dry-up of the solution can be restricted and variations in the viscosity of the solution can be restricted, which makes it possible to form the spots stably for a long period of time.

Also, in the micro array manufacturing apparatus according to the invention, when compared with in a case where the simultaneous upward and downward movement operation of the needle and solution storing portion and the upward and downward movement operation of only the needle after stop of the solution storing portion are carried out by individual drive means, the number of drive sources included in the whole apparatus can be reduced and the number of parts involved with the drive sources can be reduced, thereby being able to attain the cost reduction of the micro array manufacturing apparatus. Also, use of the single drive source can reduce the weight of the driven portion to be driven by the delivery means, which can simplify the structure of the micro array manufacturing apparatus as well as can reduce the weight thereof. Therefore, the driven portion can be driven at a high speed by the delivery means, which makes it possible to shorten the manufacturing time of the micro array.

Also, according to the invention, the solution storing portion includes a tapered interior space. In case where the interior space of the solution storing portion is formed in a tapered manner, the solution can be held positively and, at the same time, when the needle projects from the solution storing portion, the quantity of solution moving to the needle can be controlled properly.

Further, according to the invention, in the leading end of the needle, there is formed a flat surface. Thanks to this, the deformation of the leading end portion of the needle when the leading end of the needle is contacted with the substrate can be restricted, which makes it possible to form a spot stably.

Still further, according to the invention, in the needle, there is formed a slit for holding the solution therein, which makes it possible to increase the quantity of solution that can be held.

Still further, according to the invention, there is further included washing means for washing the interior space of the solution storing portion. This eliminates the possibility that the solution held by the solution storing portion in a certain step can remain within the solution storing portion until a next step. This can prevent different kinds of solutions from being mixed together.

What is claimed is:

1. A micro array manufacturing apparatus, comprising:

a working table on which a plurality of substrates can be arranged;

a first solution storing portion for storing a solution including a living body sample;

hold means for taking in said solution from said first solution storing portion to form the spot of said solution on each of said substrates;

moving means for supporting said hold means and moving said hold means in directions where said hold means approaches and goes away from said substrates; and delivery means for supporting said moving means and delivering it in an area including said working table and said first solution storing portion to thereby give it two-dimensional coordinates;

wherein said hold means is made up of a second solution storing portion for storing said solution and a needle insertable into said second solution storing portion to allow said solution stored in said second solution storing portion to adhere onto the needle, thereby allowing said hold means to form said solution spot on each of said substrates in a given quantity;

wherein said moving means includes a support portion to be delivered by said delivery means, a first movable member capable of mounting said second solution storing portion thereon and said second solution storing portion mounted in such a manner that it can be moved with respect to said support portion in given directions where it approaches and parts away from said substrates, a second movable member capable of mounting said needle thereon and mounted so as to be movable in said given directions with respect to said first movable member, and drive means for driving said second movable member; and;

wherein said first movable member is driven in linking with said second movable member to be driven by said drive means.

2. A micro array manufacturing apparatus as set forth in claim 1, wherein a deformation of a leading end of said needle is minimized or restricted as it comes into contact with said substrate.

3. A micro array manufacturing apparatus, comprising:

a working table on which a plurality of substrates are arranged;

a first solution storing portion for storing a solution including a living body sample;

hold means for taking in said solution from said first solution storing portion to form the spot of said solution on each of said substrates;

moving means for supporting said hold means and moving said hold means in directions where it approaches and goes away from said substrates; and delivery means for supporting said moving means and delivering said moving means in an area including said working table and first said solution storing portion to provide two-dimension coordinates;

wherein said hold means includes a second solution storing portion for storing said solution and a needle insertable into said second solution storing portion to allow said solution stored in said second solution storing portion to adhere onto the needle thereby allowing said hold means to form said solution spot on each of said substrates by a given quantity; and wherein said moving means includes a base portion to be delivered by said delivery means, a first movable member capable of mounting said second solution storing portion thereon and said second solution storing portion mounted so as to be movable with respect to said base portion in given directions where it approaches and goes away from said substrates, a first restrict member for restricting the movement of said first movable member in one direction with respect to said base portion, a second movable member capable of mounting said needle thereon and mounted so as to be movable in said given directions with respect to said first movable member, a second restrict member for restricting the movement of said first movable member in the other direction opposite to said one direction with respect to said first movable member, and drive means for driving said second movable member.

4. A micro array manufacturing apparatus as set forth in claim 3, wherein a deformation of a leading end of said needle is minimized or restricted as it comes into contact with said substrate.

5. A micro array manufacturing apparatus, comprising:

a working table on which a plurality of substrates are arranged;

a first solution storing portion for storing a solution including a living body sample;

hold means for taking in said solution from said first solution storing portion to form a spot of said solution on each of said substrates;

moving means for supporting said hold means and moving said hold means in directions where said hold means approaches and goes away from said substrates; and delivery means for supporting said moving means and delivering said moving means in an area including said working table and said first solution storing portion to provide two-dimensional coordinates;

wherein said hold means comprises a second solution storing portion for storing said solution and a needle insertable into said second solution storing portion to allow said solution stored in said second solution storing portion to adhere onto the needle, thereby allowing said hold means to form said solution spot on each of said substrates in a given quantity.

6. A micro array manufacturing apparatus as set forth in claim 5, wherein a deformation of a leading end of said needle is minimized or restricted as it comes into contact with said substrate.

7. A micro array manufacturing apparatus as set forth in claim 5, wherein said second solution storing portion includes a tapered interior space.

8. A micro array manufacturing apparatus as set forth in claim 5, wherein said needle includes a flat portion formed in a substrate side leading end portion thereof.

9. A micro array manufacturing apparatus as set forth in claim 3, wherein said needle includes a slit for holding said solution therein.

10. A micro array manufacturing apparatus as set forth in claim 5, further including washing means which pours a washing solution into an interior space of said second solution storing portion to thereby wash said interior space of said second solution storing portion.

* * * * *